United States Patent
Bechara et al.

(12)

(10) Patent No.: US 6,221,954 B1
(45) Date of Patent: Apr. 24, 2001

(54) CATIONIC POLYURETHANE COMPOSITIONS, QUATERNARY AMMONIUM SALTS AND METHODS FOR THEIR PREPARATION

(75) Inventors: Ibrahim Bechara, Naperville; Thomas R. Baranowski, Chicago, both of IL (US)

(73) Assignee: Witco Corporation, Greenwich, CT (US)

( * ) Notice: Subject to any disclaimer, the term of this patent is extended or adjusted under 35 U.S.C. 154(b) by 0 days.

(21) Appl. No.: 08/456,655

(22) Filed: Jun. 5, 1995

Related U.S. Application Data

(63) Continuation of application No. 08/334,450, filed on Nov. 4, 1994, now abandoned, which is a continuation of application No. 08/159,042, filed on Nov. 29, 1993, now abandoned, which is a continuation of application No. 07/786,393, filed on Nov. 1, 1991, now abandoned.

(51) Int. Cl.$^7$ ................................ C08J 3/00; C08K 3/20; C08L 75/00; C07C 211/00
(52) U.S. Cl. ................ 524/591; 524/590; 524/839; 524/840; 564/286; 564/294; 564/281
(58) Field of Search ................................ 564/286, 294, 564/281; 524/590, 591, 839, 840

(56) References Cited

U.S. PATENT DOCUMENTS 4,305,858 * 12/1981 Reischl ................................ 528/48

* cited by examiner

*Primary Examiner*—Patrick D. Niland
(74) *Attorney, Agent, or Firm*—Cook, Alex, McFarron, Manzo, Cummings & Mehler, Ltd.

(57) ABSTRACT

The preparation and use of quarternized bis hydroxy alkyl amines by the reaction of a tertiary amine and an alkylene oxide in a strong acid system are disclosed. Cationic polyurethane compositions containing pendent hydroxy alkyl groups and methods for their preparation are also disclosed.

9 Claims, No Drawings

CATIONIC POLYURETHANE COMPOSITIONS, QUATERNARY AMMONIUM SALTS AND METHODS FOR THEIR PREPARATION

This application is a continuation application of Ser. No. 08/334,450 filed Nov. 4, 1994 which is a continuation of Ser. No. 08/159,042 filed Nov. 29, 1993 which is a continuation of Ser. No. 07/786,393 filed Nov. 1, 1991 in the name of Bechara et al. all of which are now abandoned.

BACKGROUND AND DESCRIPTION OF THE INVENTION

This invention relates to processes for the manufacture of cationic polyurethane compositions and quaternary ammonium salts and to the new compositions prepared thereby. In particular this invention relates to the use of alkylene oxides to prepare cationic polyurethane compositions and quaternary ammonium salt intermediates. An important aspect of the present invention is the use of alkylene oxides such as ethylene oxide and propylene oxide to form cationic ammonium moieties in polyurethanes.

It has been known for some time that water dispersible polyurethane compositions can be prepared and used to form films. Various procedures have been disclosed in the literature for making polyurethanes water soluble without diminishing the film forming capabilities of the polyurethanes.

U.S. Pat. No. 3,470,310 (Dietrich et al.) describes the preparation of water dispersions of polyurethanes which contain salt type groups bonded into the polyurethane.

U.S. Pat. No. 3,873,484 (Bluestein et al.) discloses aqueous dispersions of polyurethanes prepared from a quaternized polyurethane prepolymer prepared by reacting from 0.6 to 1.2 equivalents of an alkoxylated diol; one hydroxyl equivalent of an N-alkyl dialkanolamine; about 4 equivalents of an organic diisocyanate and quaternizing with 0.5 equivalents of a dialkyl sulfate quaternizing agent. This quaternized polyetherurethane is chain extended to form a polyurethane-urea and dispersed in water in the presence of a nonionic surfactant belonging to the class of alkoxylated long chain alkyl phenols having an HLB of between about 14 and 16.

The use of dialkyl sulfates, such as dimethyl sulfate, and alkyl halides, such as chloroacetoamide, to quaternize tertiary nitrogen atoms is well known. These compositions, however, possess undesirable characteristics limiting their use in the preparation of cationic polyurethanes.

Dimethyl sulfate, an often used dialkyl sulfate, is highly toxic and difficult to use on a large scale. Alkyl halides such as chloroacetamide are corrosive and require the use of expensive equipment, such as special types of stainless steel.

Therefore a general object of the present invention is to provide a method of preparing cationic polyurethane compositions.

Another object of the present invention is to provide a method of preparing quaternary ammonium salt intermediates.

Another object of the present invention is to provide a process for the preparation of quaternary amines containing reactive hydroxyl groups by a method that avoids the use of corrosive or toxic reactants.

Another object of the present invention is to provide new quaternized polyurethane compositions.

Another object of the present invention is to provide water dispersible polyurethane polymers.

Another object of the present invention is to provide polyurethane compositions that form stable films.

Other objects of the present invention will become apparent from the ensuing description.

SUMMARY OF THE INVENTION

A quaternary ammonium salt is prepared by reacting a tertiary amine, particularly a hydroxyalkyl substituted dialkylamine, with a slight molar excess of an alkylene oxide in the presence of a strong acid. The reaction product, N-di(hydroxyalkyl) N-dialkyl quaternary ammonium salt can be used to prepare other compounds such as polyurethanes by reacting the quaternized bis hydroxy alkyl amine with a molar excess of a polyisocyanate and chain extending the resulting prepolymer with an active hydrogen containing compound such as an amine or water to form a stable latex. Alternatively a polyurethane composition containing tertiary amine moieties can be reacted with a molar excess of an alkylene oxide in the presence of a strong acid to form a cationic polyurethane with pendent hydroxy alkyl groups which can then be chain extended to form a stable dispersion.

DETAILED DESCRIPTION

The present invention is directed to a method for forming quaternary ammonium salts by reacting a tertiary amine moiety with an excess of an alkylene oxide in a system comprising a strong acid. More particularly, the present invention provides methods for forming isocyanate reactive quaternary ammonium compounds. These quaternary compounds are of particular value in the preperation of cationic polyurethanes. Additionally, the present invention provides methods for the synthesis of novel cationic polyurethanes containing pendent hydroxy alkyl groups from polyurethanes containing tertiary nitrogen groups.

The present invention provides new quaternary ammonium salts. These compositions are represented by the following formula:

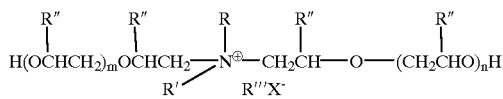

I wherein R and R' are each independently selected from, in general, alkyl groups having from 1 to about 10 carbon atoms, phenyl, and substituted phenyl groups; the carbon atoms can be linear, in the form of cyclical rings of hydrocarbons or can be heterocyclic; preferably R and R' will be alkyl groups having about 1 to 4 carbon atoms and more preferably R and R' will be methyl or ethyl groups;

R" is selected, in general, from hydrogen, alkyl groups having from 1 to about 10 carbon atoms, cycloalkyl groups having from 5 to 7 carbon atoms in the cycloalkyl group and aryl groups; preferably R" is H or methyl;

R'" is, in general, selected from hydrogen, methyl, ethyl, phenyl, aryl, and substituted alkyls such as cyano or nitro substituted alkyls and the like;

m and n are integers independently selected from 0 to about 15; and,

X is the ion of a strong acid, i.e., an acid having a $pK_a<3$ such as F$^-$, Br$^-$, Cl$^-$, SO$_3^-$, NO$_3^-$, COO$^-$ etc., with SO$_3^-$ being preferred.

The quaternary ammonium salts represented by Formula I can be prepared by reacting a tertiary amine with a molar excess of an alkylene oxide having the structural formula:

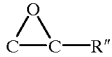

II (wherein R" is as previously defined) in the presence of a relatively strong acid.

Preferred alkylene oxides are ethylene oxide and propylene oxide. In order for the product to be useful in the present invention, in general, the acid used to prepare the quaternary ammonium intermediate should have a $pk_a$ of about 3 or less. Examples of useful acids are nitric, methane sulfonic, sulfuric, p-toluene sulfonic, cyano acetic, nitrophenylacetic, hydrohalide acids such as hydrochloric, and the like.

The tertiary amine reactant used in the present method can be selected from amines having various substituents depending upon the desired end use of the quaternary ammonium salt product. Where the product is to be used in the preparation of cationic polyurethane compositions, tertiary amines having the following structural formula are preferred:

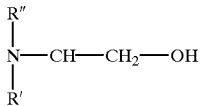

III wherein R, R' and R" are as previously defined.

The extent to which a molar excess of alkylene oxide is used in the reaction will determine to some degree the size of the molecule. In general, increasing the amount of alkylene oxide increases the number of oxide groups in the product. Thus by use of large excesses of an alkylene oxide, quaternary ammonium salts wherein m and n in Formula I are up to about 15 can be obtained. This reaction can conveniently be performed at temperatures between about 50° C. and about 100° C., although higher or lower temperatures can be used. This reaction can be performed in water or in any polar organic solvent such as dimethyl sulfoxide, N-methyl pyrolidone and ethylene glycol. Water is the preferred solvent.

The following examples illustrate the preparation of the quaternized ammonium salts and the preparation of cationic polyurethanes therefrom.

EXAMPLE 1

Preparation of a Quaternary Ammonium Salt

Dimethylethanolamine (89 grams) was added to water (207 grams) to prepare a 30 weight percent solution. Ethylene oxide (52.8 grams) was added to this aqueous amine mixture in a reaction vessel equipped with dry ice condenser, thermometer and stirrer. This addition caused a 75° C. exotherm. After the mixture was cooled to room temperature, a methane sulfonic acid solution (70%) was added slowly to lower the Ph of the reaction mixture to about 5. Mixing was continued for 2 additional hours after completion of the addition of the methane sulfonic acid and then the mixture was cooled to 28° C. The water was removed on a rotovac at 75° C. under reduced pressure. The oily semicrystalline residue was analyzed by nuclear magnetic resonance and found to be substantially N,N-bis(hydroxyethyl) N,N-dimethyl quaternary ammonium methane sulfonate having the structural formula:

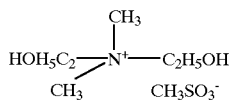

IV

Also present in the product were minor amounts of quaternary ammonium salt of the formula:

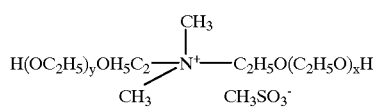

V wherein x and y are each a number from 0–15.

The same preparation was made by an alternate method by first neutralizing the aqueous tertiary amino with the acid followed by the addition of ethylene oxide. In this method, the higher ethoxylated products were kept to a minimum. The reaction product was subjected to NMR analysis. Table 1 summarizes the results of such NMR analysis.

TABLE 1

| | Resonance Signal Ratios | | | |
|---|---|---|---|---|
| | $CH_2N^+/CH_2O$ | $CH_3N^+/CH_2O$ | $CH_3S/CH_3N^+$ | % PEG |
| RUN 1 | 0.99 | 1.4 | 0.48 | 3.9 |
| RUN 2 | 1.01 | 1.53 | 0.49 | 0.3 |
| TV* | 1.0 | 1.5 | 0.5 | 0.00 |

*TV refers to the theoretical value for structure IV.

These quaternized ammonium salts are particularly useful for the preparation of polyurethanes because they have two active hydrogen atoms which can be readily reacted with isocyanate groups to form a polyurethane. By using the present quaternary ammonium salts, cationic polyurethane compositions can be prepared directly by reaction with a polyisocyanate. Such compositions can be dispersed in water to form stable latices.

The organic polyisocyanates that can be used in this reaction can be aliphatic or aromatic polyisocyanates or mixtures thereof. When color stability is important, aliphatic polyisocyanates are preferred. In general, diisocyanates are preferred. Higher polyisocyanates can be used either alone or in combination with diisocyanates. The selection of the isocyanate or mixture of isocyanates will depend upon many factors, particularly the desired properties of the polyurethane and its ultimate use. Among polyisocyanates that can be used are diisocyanates such as 1,4-cyclohexyl diisocyanate, alpha, alpha-xylene diisocyanate, 4,4'-methylene bis(cyclohexylisocyanate), 1,4-tetramethylene diisocyanate, 1,6-hexylmethylene diisocyanate, isophosphorone diisocyanate and the like; and polyisocyanates such as 1,2,4-benzene triisocyanate, polymethylene polyphenylisocyanate, and the like. Also monoisocyanates can be used in combination with the diisocyanates and/or polyisocyanates to reduce the average functionality of the isocyanate component. Examples of useful monoisocyanates are cyclohexyl isocyanate, phenyl isocyanate and toluene isocyanate.

By the process of the present invention, a quaternary ammonium salt of a dialkanolamine prepared as shown in Example 1 can be reacted with a diisocyanate and an alkoxylated diol or triol to prepare a cationic polyurethane prepolymer. Example 2 illustrates this reaction.

EXAMPLE 2

The product of Example 1 (47 grams), polypropylene glycol having a molecular weight of about 1000 (296 grams), trimethylolpropane (4.6 grams), Irganox antioxidant (2.8 grams), Tinuvin® 328 U.V. stabilizer (1.45 g) and N-methyl pyrolidone solvent (254 grams) were placed in a reaction vessel. Desmodur W isocyanate (246.1 grams) was added to the reaction vessel and the reaction mixture was heated to 90–100° C. and maintained in that temperature range for several hours. At that time the reaction product was found to have an isocyanate content of 2.95%. Then the prepolymer of Example 2 was formed into a latex by chain extension through reaction of the residual isocyanate groups with water.

This chain extension is performed by agitation, adding the polyurethane prepolymer to the water containing a non-ionic surfactant. A semi colloidal dispersion is formed. Alternatively, the prepolymer product obtained by the reaction of excess polyisocyanate and the cationic quaternary ammonium salt (polyurethane prepolymer) can be chain extended with an active-hydrogen containing compound; such as a diamine.

Example 3 illustrates the formation of a stable latex from the cationic polyurethane prepolymer of Example 2.

EXAMPLE 3

The prepolymer prepared in Example 2 (400 grams) was added to water (500 grams) containing a non-ionic surfactant (5.0 grams) with rapid agitation to form a semi-colloidal dispersion. This dispersion was continuously mixed for an additional three hours to complete the reaction of the isocyanate groups with water. Mixing was continued until all of the isocyanate groups had been reacted. The resulting latex was found to have properties as follows:

| | |
|---|---|
| Solids | 33.2% |
| Ph | 7.4 |
| Viscosity | 110 cps |
| Appearance | Semi-clear, off-white |
| Film's tensile strength | about 3300 psi |
| Film's elongation | about 460% |

In accordance with the present invention, polyurethane prepolymers can be prepared containing other desired moieties. For instance, in accordance with the present invention, a polyester reactant containing a sufficient excess of active hydrogen atoms can be used in the reaction process of Example 2 to prepare a cationic polyurethane containing polyester moieties.

EXAMPLE 4

Example 4 demonstrates the preparation of a polyurethane containing polyester moieties rather than the polyether moieties of the polypropylene glycol reactant used in Example 2.

Witco Corporation's Formrez® 55-112 brand, neopentyl adipate polyester polyol (prepared from neopentylalcohol and adipic acid) having a hydroxyl number of about 112 (296 grams); N,N-dimethyl (N,N-bishydroxyethyl) quaternary ammonium methane sulfonate (47 grams); trimethyl propane (4.6 grams); Irganox 1010 antioxidant (2.8 grams); Tinuvin® 328 U.V. stabilizer (1.45 grams); and Desmodur W diisocyanate (246 grams) were charged to a resin kettle. The mixture was heated and held at 95–100° C. for three hours. Propylene carbonate solvent (254 grams) was then added and the reaction mixture was then heated for an additional 1.75 hours. Analysis of a sample showed 3.68% isocyanate (theoretical 3.8%). Then the prepolymer was cooled to 45° C. and 800 grams of the prepolymer were added to water (1,000 grams) at 20° C. containing as surfactant GAF's Igepal® CO-730 nonyl phenol ethoxylate (10 grams). This addition was carried out a high rate of shearing and mixing. Mixing was continued until the terminal isocyanate group of the prepolymer were completely reacted with water and the polymer was fully extended to its optimum molecular weight. The final latex was colloidal and had the following properties:

Ph—7.4

Viscosity (Brookfield)—50 cps

Solids—31.7%

A film was prepared with the aid of a wetting agent and had the following properties:

Tensile Strength—about 6830 psi

Ultimate Elongation—380%

In accordance with another aspect of the present invention, cationic quaternary ammonium salts of polyurethane prepolymers can be prepared by alternate processes. For example, cationic polyurethane compositions containing pendent hydroxyl groups of the present invention can be prepared by reacting a polyurethane prepolymer containing a tertiary amine moiety of the structural formula

wherein R is as previously defined, with an alkylene oxide reactant and a strong acid, preferably having a $pK_a$ of about 3 or less, in aqueous medium. The alkylene oxide and strong acid reactants that can be used in this reaction are substantially the same as the alkylene oxide reactants and acids useful in preparing the quaternary salts as previously discussed. The number of alkylene oxide groups in the product can be varied by controlling the amount of alkylene oxide added. The prepolymer can be chain extended as previously described by reaction with an active hydrogen containing compound such as an amine or water. For example, by adding a polyurethane prepolymer to water containing a non-ionic surfactant and sufficient acid to neutralize the tertiary nitrogen atoms and subjecting it to a shearing force, there is formed a stable emulsion which has been fully chain extended by reaction with the water. The subsequent addition of alkylene oxide and further reaction of the latex at 100–130° F. for several hours converts it to a latex with a polymeric structure containing pendent hydroxyl groups.

In accordance with the present invention, cationic latices containing pendent hydroxyl groups can also be prepared by addition of alkylene oxide to the prepolymer followed by the addition of the formed mixture to water containing strong acid. The chain extension reaction is completed by allowing the terminal NCO groups to react with water over a period of a few hours. The resulting product is a stable latex of fine particle size distribution.

The polyurethane prepolymer reactant used in these aspects of the present invention can be prepared by methods known in the art such as, for example, by the process of Bluestein et al.'s U.S. Pat. No. 3,873,484, which discloses preparation of a prepolymer from the reaction of one equivalent of an alkoxylated diol or triol; one hydroxy equivalent of a dialkanolamine and about four equivalents of a diisocyanate.

Examples of alkoxylated diols useful in the preparation of the prepolymer are polyoxyethylene and polyoxypropylene glycol, and/or an alkoxylated triol, such as polypropoxylated trimethyl propane and polypropoxylated glycerol. The presence of a triol is desirable to allow branching of the prepolymer to increase toughness of the film produced by the polyurethane product.

Examples of N-alkyl dialkanolamines useful in the preparation of the polyurethane prepolymer are N-methyldiethanolamine, N-methyl dipropanolamine, N-methyl diisopropanolamine, etc. For most purposes, the N-alkyl and N-alkanol groups can have up to about 10 carbon atoms.

The diisocyanate will be selected based on the desired final properties of the polyurethane. This component can be aromatic, such as toluene diisocyanate, diphenylmethane diisocyanate, xylene diisocyanate, etc. It can also be an aliphatic or cycloaliphatic such as 1,6-hexamethylene diisocyanate, 4,5'-dicyclohexylmethyl diisocyanate, isophorone diisocyanate, etc.

Other patents disclosing the preparation of the polyurethane prepolymers are U.S. Pat. Nos. 3,388,087 and 3,479,310 to Dietrich; U.S. Pat. No. 3,410,817 to McClellan; U.S. Pat. No. 3,565,844 to Grace et al and U.S. Pat. No. 4,147,679 to Scriven et al. The following examples illustrate the preparation of cationic polyurethane composition containing pendent hydroxy alkyl groups and their properties.

EXAMPLES 5–9

A prepolymer was prepared by charging polypropylene glycol having a molecular weight of about 1000 (225.5 grams), trimethylol propane (3.5 grams), N-methyldiethanolamine (16.7 grams) and Desmodur W. diisocyanate (187.1 grams) into a reaction vessel. Solvent (193.5 grams) consisting of a mixture of dimethyl adipate and gluterate was added to the reaction vessel. The mixture was heated to 160° F. and maintained at that temperature for 3 hours with stirring. The mixture was cooled and analyzed as having an isocyanate content of about 4 weight percent. Propylene oxide in a molar excess to the N-methyl diethanolamine in the prepolymer was added to the reaction vessel. The resulting cationic polyurethane (214.5 grams) was added to water (279.5 grams) containing a nonionic surfactant (3.5 grams) and sufficient acid to neutralize all tertiary nitrogen atoms. The mixture after being subjected to high shear became a viscous white emulsion. After being sheared for 2–5 minutes it was allowed to stand overnight at room temperature to complete the chain extension by reaction between the water and the residual isocyanate groups. This also caused complete dispersion of the cationic quaternized polyurethane polymer.

This procedure was generally followed with different acids to prepare a series of cationic polyurethane dispersions with pendent hydroxyl groups. The latices formed had the following properties:

TABLE 2

| Example | Acid | Appearance | Solids (%) | Brookfield Viscosity (CPS) | Tensile (%) | % Elongation |
|---|---|---|---|---|---|---|
| 5 | sulfuric | semi-colloidal | 30.3 | 140 | 4100 | 365 |
| 6 | hydrochloric | milky | 30.4 | 180 | 4000 | 390 |
| 7* | sulfuric | semi-colloidal | 30.4 | 140 | 3660 | 340 |
| 8 | acetic | gelled | | | | |
| 9 | phosphoric | gelled | | | | |

*The prepolymer was prepared without any organic solvents.

One of the conclusions seen from the results of the five experiments reported in Table 2 is that the cationic quaternized polyurethane compositions made by the present reaction of a polyurethane containing a quaternized ammonium moiety with an alkylene oxide should be performed in the presence of a strong acid, preferably an acid having a pK$_a$ of <3. As can be seen from Table 2, the use of weak acids such as acetic and phosphoric results in unacceptable gels and does not produce useful dispersions.

It should be noted that the cationic polyurethane prepolymer, regardless of its method of preparation, can be chain extended by reaction with an active hydrogen containing compound, particularly an amine or water. This chain extension can be performed in sufficient water to complete the chain extension. An amine catalyst, such as triethylene diamine may be added to accelerate the chain extension.

Dispersions of the quaternized polyurethane prepolymer can be made with the use of a suitable surfactant. Suitable surfactants include ethoxylated octyl phenol, ethoxylated nonyl phenol, ethoxylated dodecyl phenol, ethoxylated fatty alcohols and the like. These types of surfactants are made and sold by Witco Corporation, such as under its trademark, "WITCONOL," and by other manufacturers. A dispersion containing 30–65 weight percent of the chain extended polyurethane is within the present invention.

The latex obtained from the present cationic quaternized polyurethane is stable at room temperature and makes excellent films.

The present invention also provides radiation curable cationic polyurethane dispersions. Example 10 illustrates the prepartion of a radiation curable waterborne cationic polyurethane dispersion in accordance with the present invention.

EXAMPLE 10

To a clean and dry resin kettle polypropylene glycol having a molecular weight of about 1000 (250 grams, 0.50 equiv.) is charged and heated to 185 degrees F. A vacuum is applied for ½ hour to remove moisture from the polyol and the kettle is then blanketed with nitrogen to prevent moisture from reentering the reactor. Trimethylol propane (3.9 grams, 0.088 equiv.), N,N bishydroxyethyl, NN dimethyl quaternary ammonium methane sulfonate (40 grams, 0.35 equiv.) (see Example 1), and dry N-methyl pyrolidone (160 grams) are added to the kettle. The reaction mixture should be cooled to about 110 degrees F. The kettle is purged with dry air and glycerol monoallyl ether (9.9 grams, 0.15 equiv.) is added to the kettle and the components are mixed well.

While purging with air and mixing, Desmodur W. diisocyanate (286 grams, 2.18 equiv.) and about 20 to 30 drops of dibutyl tin dilaurate catalyst are added to the kettle. The reactor is reheated to 160–180 degrees F. for 2–3 hours and the reaction mixture is analyzed for per cent NCO using standard analytical methods. When the per cent NCO is equal to or slightly below the theoretical value, hydroxy propyl acrylate (143 grams, 1.1 equiv.) and phenothiazine (90.06 grams, 75 ppm) are added and the mixture is heated and mixed under dry air until the NCO groups are substantially reacted. When the NCO groups are substantially reacted, the prepolymer is added with vigorous agitation to about 2000 grams of cold water containing 0.5 per cent p-nonylphonol ethoxylate surfactant such as Witco Chemical Corporation's Witconol NP150 surfactant. Agitation is continued for at least one hour. The resulting product is a stable latex containing polymerizable unsaturated groups.

The latex of Example 10 can be prepared for radiation curing by adding with vigorous agitation 300 grams of the latex to 0.5 parts of benzophenone, 0.1 parts of Ionol, 1.0 parts of an additive such as Union Carbide's Silwet L-7002 nonionic silicone glycol copolymer surfactant and optionally 10–20 parts of an ethylenically unsaturated monomer such as hexane diacrylate. A film can be drawn down by standard methods and dried so it will have 3 mils or less thickness. The film can be radiation cured by standard techniques such as by subjecting the film to about 300 m watts sec cm-2 for a sufficient time to yield a coating of good properties.

The cationic polyurethane compositions of the present invention have many valuable uses. For instance, aqueous dispersion or latex products of this invention are advantageously employed as coating compositions, for which purpose they may be further diluted with water and/or organic solvents, or they may be supplied in more concentrated form by evaporation of water and/or organic components of the liquid medium. As coating compositions they may be applied to any substrate including wood, metals, glass, cloth, plastics, foamed plastics and the like, by any conventional method including brushing, dipping, flow coating, spraying, and the like. The compositions may contain other conventional ingredients including organic solvents, pigments, dyes, emulsifiers/surfactants, thickeners, heat stabilizers, leveling agents/anticratering agents, fillers, sedimentation inhibitors, UV absorbers, antioxidants and the like introduced at any stage of the production process.

These latices are preferably applied to substrates in effective film-forming amounts depending on the solids content of the latex, temperature and other conditions, the type of substrate, product desired, etc. The film coating on the substrate may simply be protective, decorative, or the like or serve as an adhesive or other function. Self-supporting thin or thick films or sheets may be produced by applying the latex to a substrate with a release surface from which the cured, hardened film can be removed. Hardening and curing on the substrate is generally accomplished by simply drying under ambient conditions, which may if desired be expedited and/or facilitated by concurrent heating, subsequent baking, etc. The latices of this invention have good storage-stability and yield films and coatings with improved properties such as resistance to water, organic solvents and environmental conditions; flexibility; elasticity and/or tensile strength; and the like.

Other uses for these quaternary compounds are antistatic additives, surface active agents and/or thickeners. This is a particularly important use in the case of cationic polyurethanes containing many pendent hydroxy alkyl groups.

Another important use of the quaternized polyurethane containing pendent hydroxyl groups is its use as a coreactant in the production of polyurethane foams. In accordance with this aspect of the invention polyyurethane foams can be prepared by reacting from 1 to 70 weight percent of the quarternary polyurethane containing pendent hydroxyl groups with the desired isocyantes and the other standard components used in the production of polyurethane foams according to conventional processing techniques. The use of the quaternary ion as a coreactant imparts improved properties to the resulting polyurethane foam.

What is claimed is:

1. A method for making a polyurethane prepolymer comprising the steps of (1) reacting a N-monoalkanol tertiary amine with alkylene oxide in the presence of a strong acid having a pKa <3 to form a polyol salt having the structure

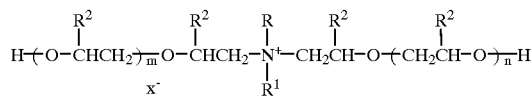

wherein R and $R^1$ are each independently selected from $C_1$–$C_{10}$ alkyl, cycloalkyl, phenyl and substituted phenyl; $R^2$ is selected from hydrogen, $C_1$–$C_{10}$ alkyl, $C_5$–$C_7$ cycloalkyl and aryl; m and n are integers independently selected from 0 to about 15; and X is selected from F, Br, Cl, $NO_3$, alkyl $SO_3$, aryl $SO_3$, $CNCH_2CO_2$, $O_2NCH_2CO_2$ and $HSO_4$ (2) reacting the polyol salt with an excess amount of an organic polyisocyanate alone or in combination with other polyols; and (3) thereafter, chain extending the product obtained with an active hydrogen-containing compound until removal of any residual isocyanate functionality is substantially complete.

2. The method of claim 1, wherein said organic polyisocyanate comprises a diisocyanate.

3. The method of claim 1, wherein said active hydrogen-containing compound comprises water.

4. The method of claim 1, wherein step (2) is carried out in the presence of a polyol comprising an aliphatic triol.

5. The method of claim 4, wherein step (2) is carried out in the presence of a polyether glycol and 1,1,1-trimethylol propane.

6. The method of claim 1, wherein step (2) is carried out in the presence of a polyol comprising a polyether polyol.

7. The method of claim 1, wherein step (2) is carried out in the presence of a polyol comprising a hydroxy terminated polyester.

8. The method of claim 1, wherein the tertiary amine in step (1) comprises N,N-dimethyl ethanolamine.

9. A method for making a polyurethane prepolymer comprising the steps of (1) reacting N,N-dimethyl ethanolamine with ethylene oxide in the presence of a strong acid having a pKa <3 and (2) reacting the product of step (1) with an excess amount of an organic polyisocyanate alone or in combination with other polyols.

* * * * *